United States Patent [19]

Choi et al.

[11] Patent Number: 5,516,761
[45] Date of Patent: May 14, 1996

[54] POUR-ON FORMULATIONS CONTAINING POLYMERIC MATERIAL

[75] Inventors: Hoo-Kyun Choi, Blue Bell; James B. Williams, Landsdale, both of Pa.

[73] Assignee: Merck & Co., Inc., Rahway, N.J.

[21] Appl. No.: 333,936

[22] Filed: Nov. 3, 1994

Related U.S. Application Data

[63] Continuation of Ser. No. 59,699, May 10, 1993, abandoned.

[51] Int. Cl.$^6$ ........................................ A61K 31/70
[52] U.S. Cl. ................................ 514/30; 514/947
[58] Field of Search ........................ 514/30, 947

[56] References Cited

U.S. PATENT DOCUMENTS

| | | | |
|---|---|---|---|
| 3,852,416 | 12/1974 | Grubb et al. | 424/411 |
| 3,950,360 | 4/1976 | Aoki et al. | 549/264 |
| 4,172,904 | 10/1979 | Young et al. | 427/4 |
| 4,173,571 | 11/1979 | Chabala et al. | 549/264 |
| 4,199,569 | 4/1980 | Chabala et al. | 514/30 |
| 4,310,519 | 1/1982 | Albers-Schonberg et al. | 514/30 |
| 4,808,615 | 2/1989 | Ott et al. | 514/89 |
| 4,873,224 | 10/1989 | Linn et al. | 514/30 |
| 4,916,120 | 4/1990 | Röben et al. | 514/30 |

FOREIGN PATENT DOCUMENTS

| | | |
|---|---|---|
| 0045655A3 | 2/1982 | European Pat. Off. . |
| 0051786A1 | 5/1982 | European Pat. Off. . |
| 0120286A1 | 10/1984 | European Pat. Off. . |
| 0137627A3 | 4/1985 | European Pat. Off. . |
| 0146414A3 | 6/1985 | European Pat. Off. . |
| 0193347A3 | 9/1986 | European Pat. Off. . |
| 0249409A3 | 12/1987 | European Pat. Off. . |
| 0329460A2 | 8/1989 | European Pat. Off. . |
| 0432494A2 | 6/1991 | European Pat. Off. . |
| 2599220 | 12/1987 | France . |

*Primary Examiner*—Marianne M. Cintins
*Assistant Examiner*—K. Weddington
*Attorney, Agent, or Firm*—Sylvia A. Ayler; Mark R. Daniel

[57] ABSTRACT

There is disclosed a topical multiple-point-application formulation containing a solution of a polymeric material and an avermectin compound (active ingredient) which has been discovered to provide superior efficacy against ectoparasites, such as fleas and ticks and endoparasites such as nematodes and heartworms, when compared to conventional formulations. The formulation contains the avermectin active ingredient and up to 50% of the polymeric material.

5 Claims, No Drawings

POUR-ON FORMULATIONS CONTAINING POLYMERIC MATERIAL

This is a continuation of application Ser. No. 08/059,699 filed on May 10, 1993; now abandoned.

BACKGROUND OF THE INVENTION

The avermectin series of compounds are potent anthelmintic and antiparasitic agents against internal and external parasites. The natural product avermectins are disclosed in U.S. Pat. No. 4,310,519 to Albers-Schonberg et al., and the 22,23-dihydro-avermectin compounds are disclosed in Chabala et al., U.S. Pat. No. 4,199,569. Administration of the avermectin compounds occur orally, parenterally or topically.

Conventional topical formulations available for use, such as sprays, dips, powders, shampoos and the like do not provide acceptable extended efficacy against ectoparasites, especially against fleas and ticks. These formulations fail because the animals are readily reinfested by fleas and ticks after treatment with the above-noted conventional formulations simply by returning to a flea infested environment. Additionally, the use of shampoos, dips and spray formulations are not very convenient to apply, and have the potential to create environmental waste problems. Further, topical formulations of currently available medicinal agents have not demonstrated efficacy against endoparasites, such as heartworms and nematodes.

It is known in the pet care industry that sustained release of an insecticide is obtained by incorporation of the insecticide into a polymeric system. However, conventional polymer based formulations rely on the vaporization of the active compounds, which means this type of system may not be used for non-evaporable drugs. See U.S. Pat. Nos. 3,852,416 and 4,172,904.

SUMMARY OF THE INVENTION

This invention is concerned with topical pour-on formulations which contain the non-evaporable active ingredient avermectin and the polymeric material, polyvinylpyrrolidone, which provides superior extended efficacy against ectoparasites, especially fleas and ticks; for a full four weeks, as well as efficacy against endoparasites, especially heartworms amd nematodes, of domestic animals particularly household pets such as cats and dogs. The formulations are prepared using a solvent such as water, or an alcohol such as ethanol, methanol, isopropanol and the like, a polymer such as polyvinylpyrrolidone, and an avermectin compound. The drug is bound to the skin with the aid of the polymer which remains on the skin surface after the solvents have evaporated following application. Thus it is an object of this invention to describe such ectoparasitic and endoparasitic efficacy. Another object is to describe the avermectin compounds which may be employed in the formulation. A still further object is to describe how extended efficacy against ticks, fleas and heartworms is obtained. Additional objects will become apparent after a reading of the following description.

DESCRIPTION OF THE INVENTION

This invention consists of topical multiple-point-application formulations of a solvent mixture of water and/or solvents with relative high vapor pressure such as ethanol, methanol, isopropanol, acetone, and the like, most preferrably ethanol, a polymeric material such as polyvinyl pyrrolidone, polyvinyl alcohol, cellulose derivatives such as methyl cellulose, ethyl cellulose, carboxy methyl cellulose, and hydroxyethyl cellulose, and the like, most preferrably polyvinyl pyrrolidone (MW from about 20,000 to 65,000, preferrably about 45,000), skin or hair substantive protein derivatives such as hydrolyzed wheat protein, hydrolyzed animal protein, gelatin derivatives, collagen derivatives, and the like, hydroalcoholic soluble copolymers such as acrylates/t-octylpropenamide copolymer and the like, and cationic quaternary amine salts and the like, and an avermectin compound, which has been found to effectively eliminate both ectoparasites, especially fleas and ticks, and endoparasites, especially heartworms and nematodes. The polymeric material helps to keep the drug at the skin level longer by remaining on the skin surface after the solvents have evaporated following application. The remaining avermectin and polymer does not change the appearance of the animal's hair coat and the avermectin is released by diffusion and/or erosion of the polymer.

The avermectin compounds of the instant invention have the following general structure:

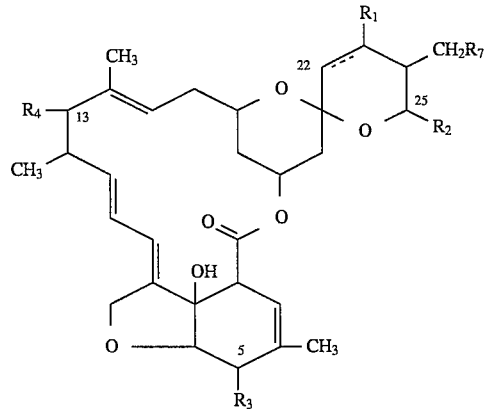

where the broken line indicates a single or a double bond at the 22,23-positions;

$R_1$ is hydrogen or hydroxy provided that $R_1$ is present only when the broken line indicates a single bond;

$R_2$ is alkyl of from 1 to 6 carbon atoms or alkenyl of from 3 to 6 carbon atoms or cycloalkyl of from 3 to 8 carbon atoms;

$R_3$ is hydroxy, methoxy or $=NOR_5$ where $R_5$ is hydrogen or lower alkyl;

$R_7$ is hydrogen, hydroxy, or lower alkyl; and $R_4$ is hydrogen, hydroxy, poly C(1–6) alkoxy or

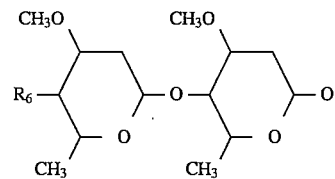

where $R_6$ is hydroxy, amino, mono- or di-$C_1$–$C_6$ alkyl amino or $C_1$–$C_6$ alkanoylamino.

The preferred compounds of the instant invention have the following structural formula:

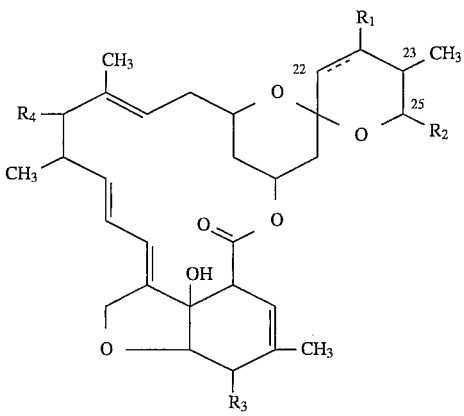

Wherein $R_1$, $R_2$, and $R_3$, are as described above, and $R_4$ is hydrogen, hydroxy, or polyalkoxy, and the broken line indicates a single or a double bond at the 22,23-position, provided that $R_2$ is hydroxy only when the broken line indicates a single bond.

The term "loweralkyl" when used in the instant application is intended to represent those alkyl groups either straight or branched chain which have from 1–5 carbon atoms. Examples of such alkyl groups are methyl, ethyl, propyl, iso-propyl, butyl, sec-butyl, pentyl, and the like.

The term "loweralkanoyl" is intended to include those alkanoyl groups containing from one to five carbon atoms in either a straight or branched chain. Examples of such alkanoyl groups are formyl, acetyl, propenyl, butyryl, valeryl, and the like.

The term "halogen" is intended to include those halogen atoms fluorine, chlorine, bromine and iodine.

The term "polyalkoxy" is intended to include methoxymethoxy, 2-methoxyethoxy, (2-methoxyethoxy)methoxy, [2-(2-methoxyethoxy)ethoxy] methoxy; and the like.

Examples of preferred compounds of the instant invention are:
4"-keto avermectin B1;
4"-keto avermectin B1;
4"-keto-22,23-dihydro avermectin B1;
4"-keto-22,23-dihydro avermectin B1;
4"-deoxy-4"-amino avermectin B1;
4"-deoxy-4"-amino avermectin B2b;
4"-deoxy-4"-amino-22,23-dihydro avermectin B1;
4"-deoxy-4"-amino-22,23-dihydro avermectin B1;
4"-deoxy-4"-acetylamino avermectin B1;
4"-deoxy-4"-acetylamino avermectin B2b;
4"-deoxy-4"-acetylamino-22,23-dihydro avermectin B1;
4"-deoxy-4"-acetylamino-22,23-dihydro avermectin B1;
4"-deoxy-4"-dimethylamino avermectin B1;
4"-deoxy-4"-dimethylamino avermectin B1;
4"-deoxy-4"-dimethylamino-22,23-dihydro avermectin B1;
4"-deoxy-4"-dimethylamino-22,23-dihydro avermectin B1;
4"-deoxy-4"-p-chloro benzenesulfonylamino-22,23-dihydro avermectin B1;
4"-deoxy-4"-p-chloro benzenesulfonylamino-22,23-dihydro-13-O-[(2-methoxyethoxy)methyl] avermectin B1 aglycone;
4"-deoxy-4"-(2-methylbenzenesulfonylamino)-avermectin B1;
4"-deoxy-4"-(2-methylbenzenesulfonylamino)-avermectin B1.
13-epi-O-(methoxymethyl)-22,23-dihydro avermectin B1 aglycone (hereinafter referred to as 13-O-MOM AVM).

The most preferred compound is 22,23-dihydro-13-O-[(2-methoxyethoxy)methyl] avermectin B1 aglycone (hereinafter referred to as 13-O-MEM AVM)).

The "b" compounds, those with a 25-iso-propyl group, are not necessarily separated from the corresponding "a" compound with a 25-sec-butyl group and the compounds are generally isolated as mixtures of the two compounds, consisting of at least 80% of the sec-butyl compound and no more than 20% of the iso-propyl compound. Thus references in the instant application to "a" compounds such as B1a, A1a, and the like, are construed to actually contain a certain proportion of the corresponding "b" compound. Alternatively, this representation of a mixture is sometimes done by referring to the B1 or B2 compounds or by separating the "a" compound from the "b" compound by a slash (/) such as B1a/B1b, B2a/B2b and the like.

Additionally, the products of synthetic procedures such as racemization or epimerization, procedures known to those skilled in the art, can be a mixture of stereoisomers. In particular, the stereoisomers at the 13- and 23-positions may be oriented either α- or β- representing such groups being below or above the general plane of the molecule, respectively. In each case, and at other positions in the molecule, both the α- and β- configurations are intended to be included within the ambit of this invention.

A related family of natural products also useful in the present invention is known as the milbemycins. The milbemycins have the same macrocyclic ring structures as the avermectins but have no substitution at position 13 and have a methyl or ethyl group at position 25 ($R_2$=methyl or ethyl rather than isopropyl or sec-butyl as in the avermectins). The milbemycins and the fermentation conditions used to prepare them are described in U.S. Pat. No. 3,950,360. Closely related 13-deoxyavermectin aglycones are prepared by chemical modification of the natural avermectins and have been described in U.S. Pat. No. 4,173,571.

In the topical forms of the avermectin formulation it has not been possible to provide a formulation which provides superior extended efficacy against ectoparasites, especially fleas and ticks. Additionally, currently available topical formulations do not provide adequate efficacy against endoparasites, especially heartworms and nematodes.

The instant formulations of an avermectin compound with a polymeric material gives the advantages of a pour-on topical formulation which provides the animal with extended effective treatment and protection against endoparasites and ectoparasites, especially fleas, ticks, mange mites, hookworms, ascarids, and heartworms. Additional advantages of this invention are that the formulation is not readily dislodgeable by petting the animals, it has good spreadability and cold temperature usage.

The instant polymeric formulation can contain the avermectin compound, alcohol, water and the polymer as the only ingredients. The formulations will generally be prepared to administer the avermectin from about 0.005 by weight to about 30% of the total composition, preferably from 0.1 to 10% by weight and most preferably about 5% by weight of the active ingredient. At a preferred dose of about 0.5 to 50 mg/kg the formulation is applied at a dose volume of 0.05 to 4.0 ml/kg body weight. The polymer is present in the compositions of the present invention in amounts ranging from about 0.01 to 20% w/v and preferrably from about 0.5 to 10% w/v by weight of the total composition and up to 95% by volume of alcohol, q.s. to 100% with water.

The preferred formulation contains in addition to the polymer, alcohol, water and avermectin compound, additional ingredients such as antioxidants and solvents. The solvents can be glycol, glycerides, glycol ethers, and the like. The anti-oxidants are generally added to the formulation at rates of from 0.005 to 1.0% (w/v) and can be propyl gallate, BHA (butylated hydroxy anisole), BHT (butylated hydroxy toluene) monothioglycerol and the like, preferrably BHT.

The formulation is prepared by dissolving the avermectin compound in the intended volume of alcohol. The antioxidant and one of the polymeric materials listed above are then dissolved in the alcohol/avermectin mixture. The volume is then adjusted to 100% by the addition of the final volume of water, with the solution being mixed until it becomes homogeneous. Alternatively, either the BHT or the polymer, or both can be added prior to the addition of the avermectin compound.

The avermectin-polymeric topical multiple-point-application formulation may be administered to warm blooded animals to provide long acting treatment and protection against endoparasites and ecotoparasites. Typically the formulation is administered to multiple points, typically 2 to 6 points, along the back of domesticated animals and household pets such as cats, dogs, and the like.

The following example is provided in order that the invention might be more fully understood. It is not to be construed as a limitation of the invention.

EXAMPLE OF THE INVENTION

The formulations of this invention which are employed depend upon the particular avermectin compound and treatment. To test the effective killing power of the compositions of the present invention against fleas and ticks, the following compositions were prepared:

| Composition I | |
|---|---|
| 13-O-MEM AVM | 0.3% w/v |
| polyvinyl pyrrolidone | 5.0% w/v |
| Cremophor RH-40 | 1.0% w/v |
| Anhyd. (Denatured)Ethanol | 40.0% v/v |
| Softigen 767 | 20.0% v/v |
| Water (q.s.) | 100.0% v/v |
| Compostion II | |
| 13-O-MEM AVM | 0.3% w/v |
| polyvinyl pyrrolidone | 5.0% w/v |
| Anhydrous Ethanol | 75.0% v/v |
| Water (q.s.) | 100.0% v/v |
| BHT | 0.01% w/v |
| Composition III | |
| 13-O-MOM AVM | 5.0% w/v |
| polyvinyl pyrrolidone | 5.0% w/v |
| BHT | 0.01% w/v |
| Anhydrous ethanol | 90.0% v/v |

-continued

| | |
|---|---|
| Water (q.s.) | 100.0% v/v |
| Composition IV | |
| 13-O-MEM AVM | 0.6% w/v |
| polyvinyl pyrrolidone | 5.0% w/v |
| Anhydrous Ethanol | 75.0% v/v |
| Vitamin E | 0.02% v/v |
| Water (q.s.) | 100.0% v/v |
| Composition V | |
| 13-O-MEM AVM | 0.6% w/v |
| hydrolyzed wheat protein | 3.0% w/v |
| Anhydrous Ethanol | 90.0% v/v |
| Vitamin E | 0.02% v/v |
| Water (q.s.) | 100.0% v/v |
| Composition VI | |
| 13-O-MEM AVM | 0.6% w/v |
| Ethocel | 2.0% w/v |
| Anhydrous Ethanol | 90.0% v/v |
| Vitamin E | 0.02% v/v |
| Water (q.s.) | 100.0% v/v |
| Composition VII | |
| 13-O-MEM AVM | 0.6% w/v |
| polyvinyl pyrrolidone | 5.0% w/v |
| Miglyol | 0.5% v/v |
| Anhydrous Ethanol | 80.0% v/v |
| Vitamin E | 0.02% v/v |
| Water (q.s.) | 100.0% v/v |
| Composition VIII | |
| 13-O-MEM AVM | 0.6% w/v |
| acrylates/t-octylpropenamide copoly | 1.0% w/v |
| polyvinyl pyrrolidone | 2.0% v/v |
| Anhydrous Ethanol | 80.0% v/v |
| Vitamin E | 0.02% v/v |
| Water (q.s.) | 100.0% v/v |

Softigen 767 is a tradename for PEG-6 caprylic/caprate glyceride, Cremophor RH-40 is a tradename for a mixture of glycerol polyethylene and glycol oxystearate, and Ethocel is a tradename for ethyl cellulose.

The compositions of the present invention were prepared in the foregoing manner: the avermectin compound is dissolved in the intended volume of anhydrous ethanol. When dissolved, the BHT and PVP are added and dissolved in the avermectin/ethanol mixture. The volume of the mixture is then adjusted to 100% (batch size 1000L) with the final volume of water and additive. The solution is mixed until it becomes homogeneous.

Each composition was topically applied in multiple locations, typically 2 to 6 points spaced equidistant between the back of the neck and the head of the tail of a flea infested dog. Counts were made by combing the hair, removing and counting the live parasites on the dog at a specified time.

The observed flea kills using Composition III, varying the amount of 13-O-MEM AVM, is given in Table No. 1 below, where 60 dogs, were allocated to four treatment groups. The dogs were infested with 100 unfed, adult fleas at times indicated by the down arrow (↓), which is equivalent to three days before a flea count is conducted. Treatment was applied on day zero.

TABLE 1

Summary of the efficacy of 13-O-MEM AVM in a vehicle containing 90% v/v Anhyd. ethanol, 5% w/v of about 45,000 MW PVP, 0.01% w/v BHT and q.s. to 100% v/v with water against fleas (*Ctenocephalides felis*) in trials 13979 and 13981

| | | 2-MEM | | | |
|---|---|---|---|---|---|
| Variable | Control | 10 mg/kg | 15 mg/kg | 20 mg/kg | 25 mg/kg |
| | Numbers of dogs treated | | | | |
| Trial 13979 | 6 | 6 | 6 | 6 | 6 |
| Trial 13981 | 6 | 6 | 6 | 6 | 6 |
| | Number of *C. felis* counted[1] (% reduction from control) | | | | |
| Day-1 ↓ | | | | | |
| Trial 13979 | 66.3 | 71.7 | 64.1 | 65.2 | 70.2 |
| Trial 13981 | 80.4 | 80.5 | 82.1 | 81.0 | 83.6 |
| Overall | 73.0 | 76.0 | 72.5 | 72.7 | 76.6 |
| Day 0 Treatment | | | | | |
| Day 3 | | | | | |
| Trial 13979 | 78.9 | 1.5 | 0.0 | 0.6 | 0.7 |
| Trial 13981 | 75.0 | 1.7 | 3.8 | 0.9 | 1.2 |
| Overall | 76.9 | 1.6 | 1.2 | 0.8 | 0.9 |
| | | (97.9%) | (98.4%) | (99.0%) | (98.8%) |
| Day 13 ↓ | | | | | |
| Day 16 | | | | | |
| Trial 13979 | 101.5 | 14.0 | 4.1 | 0.5 | 0.3 |
| Trial 13981 | 85.6 | 5.3 | 4.8 | 0.3 | 0.1 |
| Overall | 93.2 | 8.7 | 4.5 | 0.4 | 0.2 |
| | | (90.7%) | (95.2%) | (99.5%) | (99.8%) |
| Day 20 ↓ | | | | | |
| Day 23 | | | | | |
| Trial 13979 | 86.5 | 14.9 | 7.9 | 1.2 | 1.0 |
| Trial 13981 | 80.9 | 8.6 | 4.0 | 4.1 | 1.4 |
| Overall | 83.7 | 11.3 | 5.6 | 2.4 | 1.2 |
| | | (86.5%) | (93.3%) | (97.2%) | (98.5%) |
| Day 30 ↓ | | | | | |
| Day 33 | | | | | |
| Trial 13979 | 85.0 | 39.8 | 18.2 | 5.2 | 2.9 |
| Trial 13981 | 86.1 | 48.4 | 5.0 | 26.2 | 3.3 |
| Overall | 85.6 | 43.9 | 5.0 | 12.0 | 3.1 |
| | | (48.7%) | (88.6%) | (86.0%) | (96.4%) |

[1]Geometric mean, based on transformation ln(count + 1)

TICK COUNTS

| Group/ Treatment | Dog # | ↓0 | 1 | 2 | ↓14 | 15 | ↓21 | 22 | ↓28 | 29 |
|---|---|---|---|---|---|---|---|---|---|---|
| 1 | 1297 | 13 | 8 | 9 | 13 | 15 | 14 | 22 | 14 | 17 |
| Untreated | 1441 | 7 | 7 | 11 | 17 | 17 | 31 | 33 | 21 | 26 |
| Control | 1668 | 18 | 21 | 19 | 11 | 10 | 19 | 26 | 13 | 13 |
| | 1657 | 16 | 18 | 17 | 18 | 16 | 19 | 18 | 27 | 16 |
| | 1680 | 13 | 10 | 12 | 12 | 19 | 20 | 20 | 19 | 13 |
| | 1686 | 17 | 12 | 14 | 13 | 15 | 21 | 26 | 19 | 17 |
| Geometric Mean | | 13.5 | 11.8 | 13.3 | 13.8 | 15.1 | 20.1 | 23.7 | 18.3 | 16.5 |
| 2 | 1700 | 6 | 0 | 0 | 5 | 0 | 12 | 1 | 12 | 6 |
| 2-MEM | 1669 | 13 | 9 | 6 | 4 | 2 | 12 | 6 | 11 | 11 |
| EtOH/Water | 1595 | 12 | 7 | 6 | 0 | 0 | 0 | 0 | 0 | 0 |
| +PVP/Vit E | 1304 | 6 | 8 | 1 | 2 | 0 | 12 | 1 | 14 | 5 |
| 2 ml/kg | 1687 | 18 | 12 | 6 | 4 | 0 | 8 | 9 | 10 | 6 |
| | 1658 | 8 | 4 | 2 | 2 | 0 | 3 | 2 | 5 | 2 |
| Geometric Mean | | 9.7 | 5.0 | 2.6 | 2.3 | 0.2 | 5.6 | 2.1 | 6.3 | 3.7 |
| % Reduction | | — | 57.4 | 80.7 | 83.1 | 98.7 | 72.4 | 91.3 | 65.4 | 77.7 |
| 3 | 1674 | 20 | 2 | 0 | 4 | 0 | 6 | 2 | 7 | 6 |
| 2-MEM | 1314 | 10 | 2 | 0 | 0 | 0 | 2 | 0 | 0 | 0 |
| EtOH/Water | 1515 | 12 | 4 | 1 | 2 | 0 | 0 | 1 | 1 | 0 |
| +PVP/Vit E | 1274 | 13 | 0 | 2 | 2 | 0 | 7 | 5 | 10 | 12 |
| 1 ml/kg | 1553 | 9 | 3 | 3 | 0 | 0 | 13 | 6 | 4 | 2 |
| | 1303 | 12 | 8 | 2 | 1 | 0 | 19 | 10 | 9 | 9 |
| Geometric Mean | | 12.3 | 2.4 | 1.0 | 1.1 | 0 | 5.0 | 2.7 | 3.5 | 2.7 |
| % Reduction | | — | 79.4 | 92.2 | 91.9 | 100 | 75.1 | 88.4 | 80.6 | 83.4 |
| 4 | 1268 | 25 | 11 | 3 | 3 | 1 | 12 | 9 | 11 | 7 |

TABLE 1-continued

Summary of the efficacy of 13-O-MEM AVM in a vehicle containing 90% v/v Anhyd. ethanol, 5% w/v of about 45,000 MW PVP, 0.01% w/v BHT and q.s. to 100% v/v with water against fleas (*Ctenocephalides felis*) in trials 13979 and 13981

| 2-MEM | 1659 | 15 | 11 | 4 | 1 | 0 | 5 | 1 | 18 | 4 |
| EtOH/Water | 1656 | 14 | 9 | 5 | 1 | 0 | 6 | 1 | 12 | 3 |
| +PVP/BHT | 1410 | 14 | 6 | 0 | 3 | 1 | 6 | 2 | 7 | 7 |
| 2 ml/kg | 1282 | 15 | 5 | 0 | 2 | 0 | 0 | 0 | 10 | 5 |
| | 2412 | 20 | 3 | 1 | 0 | 0 | 9 | 16 | 6 | 3 |
| Geometric Mean | | 16.8 | 6.9 | 1.5 | 1.4 | 0.3 | 4.8 | 2.6 | 10.1 | 4.6 |
| % Reduction | | — | 41.3 | 88.7 | 89.8 | 98.3 | 76.1 | 89.2 | 45.1 | 72.2 |

What is claimed is:

1. A topical formulation for direct application to the skin of an animal, effective for treatment of ecto and endoparasitic infestations for four weeks, consisting of from about 0.01 to about 20% w/v of polyvinyl pyrrolidone, having a molecular weight of about 20,000 to about 65,000, from about 1 to from about 95% v/v of ethanol, 100% v/v obtained with addition of water, and from about 0.05 to from about 10% w/v of an avermectin compound having the formula:

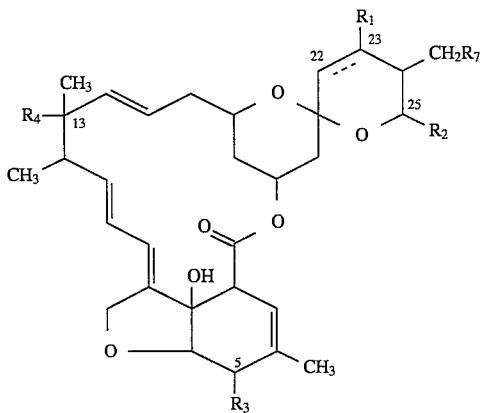

where the broken line indicates a single or a double bond at the 22,23-positions;

$R_1$ is hydrogen or hydroxy, provided that $R_1$ is present only when the broken line indicates a single bond;

$R_2$ is alkyl of from 1 to 6 carbon atoms or alkenyl of from 3 to 6 carbon atoms or cycloalkyl of from 3 to 6 carbon atoms;

$R_3$ is hydroxy, methoxy, or $=NOR_5$; where $R_5$ is hydrogen or lower alkyl;

$R_7$ is hydrogen, hydroxy or lower alkyl; and $R_4$ is hydrogen, hydroxy, poly C(1–6) alkoxy, or

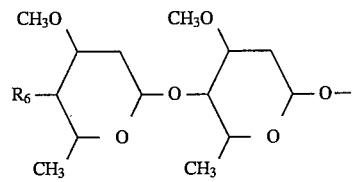

where $R_6$ is hydroxy, amino, mono- or di-$C_1$-$C_6$ alkylamino or $C_1$-$C_6$ alkanolylamino.

2. The formulation of claim 1 wherein $R_4$ is hydrogen, hydroxy or polyalkoxy.

3. The formulation of claim 1 which contains from 0.1 to 5.0% w/v of the avermectin compound and 5.0 to 10% w/v of the polyvinyl pyrrolidone and wherein $R_4$ of the avermectin compound is $CH_3OCH_2CH_2OCH_2O$.

4. The formulation of claim 1 wherein the polyvinyl pyrrolidone has a molecular weight of about 45,000.

5. A method for the treatment of internal and external parasites of animals for four weeks, which comprises applying a formulation consisting of 20% w/v of polyvinyl pyrrolidone, from about 1 to from about 95% v/v of ethanol, 100% v/v obtained with addition of water, and from about 0.05 to from about 10% w/v of an avermectin compound having the formula:

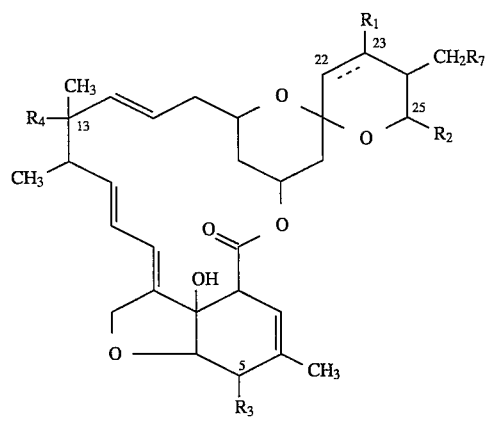

where the broken line indicates a single or a double bond at the 22,23-positions;

$R_1$ is hydrogen or hydroxy, provided that $R_1$ is present only when the broken line indicates a single bond;

$R_2$ is alkyl of from 1 to 6 carbon atoms or alkenyl of from 3 to 6 carbon atoms or cycloalkyl of from 3 to 6 carbon atoms;

$R_3$ is hydroxy, methoxy, or $=NOR_5$; where $R_5$ is hydrogen or lower alkyl;

$R_7$ is hydrogen, hydroxy or lower alkyl; and $R_4$ is hydrogen, hydroxy, poly C(1–6) alkoxy, or

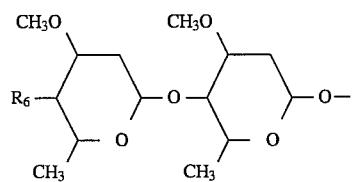

where $R_6$ is hydroxy, amino, mono- or di-$C_1$-$C_6$ alkylamino or $C_1$-$C_6$ alkanolylamino, to two to six points on the skin, along the back, of the animal.

* * * * *